(12) United States Patent
Lopez Quintela

(10) Patent No.: US 9,302,322 B2
(45) Date of Patent: Apr. 5, 2016

(54) LUMINESCENT NANOCOMPOUNDS

(71) Applicant: NANOGAP SUB NM POWDER, S.A., Ames (ES)

(72) Inventor: Manuel Arturo Lopez Quintela, Santiago de Compostela (ES)

(73) Assignee: NANOGAP SUB NM POWDER, S.A., Coruna (ES)

( * ) Notice: Subject to any disclaimer, the term of this patent is extended or adjusted under 35 U.S.C. 154(b) by 0 days.

(21) Appl. No.: 14/650,522

(22) PCT Filed: Dec. 11, 2013

(86) PCT No.: PCT/EP2013/076178
§ 371 (c)(1),
(2) Date: Jun. 8, 2015

(87) PCT Pub. No.: WO2014/090853
PCT Pub. Date: Jun. 19, 2014

(65) Prior Publication Data
US 2015/0321252 A1    Nov. 12, 2015

(30) Foreign Application Priority Data

Dec. 12, 2012 (EP) .................................... 12382495

(51) Int. Cl.
*G01N 15/06* (2006.01)
*G01N 33/00* (2006.01)
*G01N 33/48* (2006.01)
(Continued)

(52) U.S. Cl.
CPC ............. *B22F 1/0044* (2013.01); *B22F 1/0088* (2013.01); *C09K 11/58* (2013.01); *G01N 21/6428* (2013.01); *B82Y 20/00* (2013.01); *G01N 2201/068* (2013.01); *Y10S 977/95* (2013.01)

(58) Field of Classification Search
CPC ........ B32B 15/01; C25D 15/00; G01N 21/64; G01N 15/06; G01N 33/00; G01N 33/48; B05D 1/18
USPC ................................ 422/68.1, 82.05; 428/615
See application file for complete search history.

(56) References Cited

U.S. PATENT DOCUMENTS

| 4,283,382 A | 8/1981 | Frank et al. |
| 7,465,747 B2 | 12/2008 | Matsumoto et al. |

(Continued)

FOREIGN PATENT DOCUMENTS

| EP | 1914196 A1 | 4/2008 |
| EP | 2206503 A1 | 7/2010 |

(Continued)

OTHER PUBLICATIONS

Abad, J., et al., "Synthesis of omega-hydroxy hexathiolate-protected subnanometric gold clusters", "J. Am. Chem. Soc.", Oct. 6, 2007, pp. 12932-12933, vol. 129.
(Continued)

*Primary Examiner* — Brian J Sines
(74) *Attorney, Agent, or Firm* — Hultquist, PLLC; Steven J. Hultquist

(57) ABSTRACT

The present invention relates to nanocompounds comprising a charge-transfer complex of at least two different size metal atomic quantum clusters (AQCs) and the use thereof as luminescent nanocompounds, particularly for the use thereof as fluorescent nanocompounds; as well as the method for obtaining and detecting them.

18 Claims, 4 Drawing Sheets

(51) Int. Cl.
*B32B 15/01* (2006.01)
*C25D 15/00* (2006.01)
*B22F 1/00* (2006.01)
*G01N 21/64* (2006.01)
*C09K 11/58* (2006.01)
*B82Y 20/00* (2011.01)

(56) References Cited

U.S. PATENT DOCUMENTS

| | | | |
|---|---|---|---|
| 8,696,786 B2* | 4/2014 | Lopez Quintela et al. | 75/370 |
| 2002/0021003 A1 | 2/2002 | McGrew | |
| 2008/0265176 A1 | 10/2008 | Chauhan et al. | |
| 2009/0035852 A1* | 2/2009 | Lopez Quintela et al. | 435/375 |
| 2010/0215766 A1* | 8/2010 | Lopez Quintela et al. | 424/618 |
| 2010/0224831 A1 | 9/2010 | Woo et al. | |
| 2011/0305919 A1 | 12/2011 | Conroy et al. | |
| 2012/0315495 A1* | 12/2012 | Lopez Quintela | 428/463 |
| 2014/0318980 A1* | 10/2014 | Lopez Quintela et al. | 205/340 |
| 2015/0064604 A1* | 3/2015 | Jonke et al. | 429/506 |

FOREIGN PATENT DOCUMENTS

| | | |
|---|---|---|
| EP | 2457572 A1 | 5/2012 |
| EP | 2505616 A2 | 10/2012 |
| WO | 2007070115 A1 | 6/2007 |
| WO | 2012090034 A1 | 7/2012 |

OTHER PUBLICATIONS

Calvo Fuentes, J., et al., "Synthesis of Subnanometric Metal Nanoparticles", "Encyclopedia of Nanotechnology", Jul. 1, 2012, pp. 2639-2648, Publisher: Springer Netherlands.

Douliez, J., et al., "Synthesising gold nanoparticles within bola fatty acid nanosomes", "Journal of Colloid and Interface Science", May 27, 2009, pp. 610-613, vol. 337.

Huhtinen, P., et al., "Synthesis, characterization, and application of Eu(III), Tb(III), Sm(III), and Dy(III) lanthanide chelate nanoparticle labels", "Analytical Chemistry", Apr. 15, 2005, pp. 2643-2648, vol. 77, No. 8.

Resch-Genger, U., et al., "Nanocrystals and Nanoparticles Versus Molecular Fluorescent Labels as Reporters for Bioanalysis and the Life Sciences: A Critical Comparison", "Advanced Fluorescence Reporters in Chemistry and Biology II", Jul. 3, 2010, pp. 3-40, vol. 9, Publisher: Springer Berlin Heidelberg.

Sardar, D., et al., "Rare Earth-Doped Nanocrystals for Biosensing and Imaging", "Biophotonics International", 2008, pp. 45-48, vol. 15.

Shichibu, Y., et al., "Large-scale synthesis of thiolated Au25 clusters via ligand exchange reactions of phosphine-stabilized Au11 clusters", "J. Am. Chem. Soc.", Sep. 8, 2005, pp. 13464-13465, vol. 127.

* cited by examiner

LUMINESCENT NANOCOMPOUNDS

CROSS-REFERENCE TO RELATED APPLICATIONS

This application is a U.S. national phase under the provisions of 35 U.S.C. §371 of International Patent Application No. PCT/EP13/76178 filed Dec. 11, 2013, which in turn claims priority of European Patent Application No. 12382495.5 filed Dec. 12, 2012. The disclosures of such international patent application and European priority patent application are hereby incorporated herein by reference in their respective entireties, for all purposes.

FIELD OF THE INVENTION

The present invention relates to charge-transfer (CT) complexes of metal atomic quantum clusters (AQCs), optionally coordinated with organic ligands, to their method of obtention and to the use thereof as luminescent nanocompounds, particularly for the use thereof as fluorescent nanocompounds.

BACKGROUND

Today, the use of fluorescence techniques such as fluorescence spectroscopy, fluorescence microscopy, flow cytometry or in vivo fluorescence imaging, allows the fast, clear, reliable and simple detection of the interaction between biomolecules, or the interaction of these biomolecules with other inorganic or organic molecules, such as drugs, for example. These techniques require the measurement of certain experimental parameters such as the excitation wavelength ($\lambda_{exc.}$), the emission wavelength ($\lambda_{em.}$), the intensity or quantum yield, the mean lifetime, and the fluorescence anisotropy.

A fluorescent probe suitable to be used as a nanosensor or bioprobe in drug discovery, genetic analysis, flow cytometry or high performance screening should have the following properties: it must be able to be excited without affecting the matrix it surrounds, easily detected, has a high quantum yield, is adaptable to the medium, for example, a cell culture, is stable and has functional groups which allow molecular labeling. It can also be favorable for these luminescent probes to have a long mean lifetime, to be non-toxic and that the luminescence parameters thereof are reproducible over time.

Today, the only fluorescent systems known having huge Stokes shifts of greater than 200 nm and slow decaying times of more than a microsecond are based on rare earth ions. However, they present multiple drawbacks such as: the difficulty in incorporating the same in matrices such that they do not lose their fluorescent characteristics; the existence of fixed and particular excitation, emission and Stokes shift characteristics corresponding to each rare earth, therefore they are not susceptible to being changed, and they are expensive and scarce materials. Examples of these systems are described in Sardar, D. K. et al., *Biophotonics*, January 2008; Resch-Genger, U., *Advanced Fluorescence Reporters in Chemistry and Biology II Springer Series on Fluorescence*, 2010, Volume 9, Part 1, 3-40; Harma H. et al., *Analytical Chemistry*, 2005, 77, 2643-2648; US7465747B2; US 2010/0224831 A1 and U.S. Pat. No. 4,283,382.

Therefore, it would be necessary to find luminescent probes that overcome these drawbacks of the nanoparticles based on rare earth elements.

BRIEF DESCRIPTION OF THE INVENTION

Surprisingly, the authors of the present invention have discovered fluorescent nanocompounds in the form of charge-transfer complexes of AQCs with huge Stokes' shifts and decaying times much greater than those described in the state of the art which do not use rare earth elements. The nanometric size of these complexes favors its use in a wide number of applications. Furthermore, its method of synthesis, allows the inventors to select the size of the AQCs, i.e. to select the excitation and emission wavelengths, and therefore to select the desired Stokes shift for each application as a fluorescent compound.

Therefore, one aspect of the invention refers to these nanocompounds which comprise a charge-transfer complex of at least two different size metal atomic quantum clusters (AQCs), $M_n$ and $M'_{n'}$, of formula (I):

$$M_n^+ M'_{n'}^- \qquad (I),$$

wherein the metals, M and M', of the metal AQCs are the same or different metals, $M_n$, is the smaller AQC which is present in its oxidized form, $M_n^+$, $M'_{n'}$, is the larger AQC which is present in its reduced form, $M'_{n'}^-$, $M_n^+$ and $M'_{n'}^-$ are bound by electrostatic interactions, n and n' are respectively the number of metal atoms of M and M', and n is smaller than n'.

In one embodiment the metals, M and M', of the metallic AQCs are selected from transition metals or combinations thereof, preferably the transition metals are selected from the group consisting of Au, Ag, Co, Cu, Pt, Fe, Cr, Pd, Ni, Rh and combinations thereof, more preferably they are selected from the group consisting of Au, Ag, Cu and combinations thereof, and more preferably the transition metals are selected from the group consisting of Au, Ag and the combination thereof.

In another embodiment the number of metal atoms, n and n', of the at least two different size metal atomic quantum clusters are:

between 2 and 309 metal atoms,
between 2 and 102 metal atoms,
between 2 and 55 metal atoms, and
between 2 and 25 metal atoms.

In a further embodiment the difference between n and n' is between 5 and 50 atoms or between 5 and 25 atoms.

In a preferred embodiment the charge-transfer complex is additionally bound to organic ligands, preferably selected from ω-hydroxyacids and ω-mercaptoacids ligands, which are attached to the atomic quantum clusters, $M_n$ and $M'_{n'}$.

Another aspect the invention refers to the use of a charge-transfer complex as defined above, as a luminescent nanocompound.

In one embodiment the luminescence is obtained after an excitation of the charge-transfer complex by an external excitation source.

In a preferred embodiment the luminescence is fluorescence.

In another embodiment the Stokes shift which produces the luminescence is greater than approximately 150 nm, preferably greater than 300 nm.

In a further embodiment the luminescence has a decaying time greater than 0.1 µs, preferably greater than 1 µs.

In a further aspect, the present invention relates to a method for detecting a charge-transfer complex as defined above comprising the steps of:

a) exciting the charge-transfer complex with an external excitation source at a predetermined excitation wavelength ($\lambda_{exc.}$) and b) detecting one or more of the following parameters:
emission wavelength ($\lambda_{em.}$),
intensity,
mean lifetime,
anisotropy,
of said charge-transfer complex by suitable detection means.

In another further aspect the invention relates to a method for obtaining a charge-transfer complex as defined above which comprises the steps of:
  a) preparing an aqueous solution of the smaller AQC,
  b) preparing an aqueous solution of the larger AQC, and
  c) mixing together the aqueous solution of the smaller AQC with the aqueous solution of the larger AQC.

In another aspect the invention relates to a method for obtaining a charge-transfer complex which is additionally bound to organic ligands, preferably the organic ligands are selected from ω-hydroxyacids and ω-mercaptoacids ligands which are attached to the atomic quantum clusters $M_n$ and $M'_{n'}$, wherein the method comprises the steps of:
  a) preparing a nanosome by mixing ω-hydroxyacids and ω-mercaptoacids in the presence of a base in aqueous medium,
  b) adding at least one metal salt to the mixture prepared in step a), and
  c) reducing the mixture obtained in step b), and
  d) breaking the nanosomes present in the mixture obtained in step c).

In one preferred embodiment the step of breaking the nanosomes is made by means of ultracentrifugation.

These nanocompounds achieve high quantum yields which are greater than those obtained with the rare earth-based systems.

The excitation and emission wavelengths depend on the size of the AQCs present in the charge-transfer complex. The excitation and emission wavelengths can be selected at will directing the formation of AQCs of necessary sizes. Thus, the Stokes shift to be obtained can be selected at will, thus releasing the fixed and particular imposition that exists in rare earth-based fluorescence methods. Furthermore, due to the characteristics of the AQCs used there is no photobleaching.

Metal transition elements such as Au or Ag, for example, which are not toxic when present in very low concentrations, can be used. Furthermore, the great natural abundance of these elements makes this a completely sustainable method. The luminescent nanocompounds, i.e. the charge-transfer complexes bound or not to organic ligands, synthesized:
  are stable without loss of their properties over a period of at least one year stored under natural light and room temperature,
  are stable in the pH range of 3 to 10,
  can be concentrated until dry without losing their fluorescents properties even in dried form,
  can be redissolved once dried without losing their fluorescents properties, and also
  are used at a concentration less than that used in rare earth element-based luminescent systems.

The charge-transfer complex may be additionally bound to organic ligands, which can be further functionalized in its outer surface for the use thereof in different environments. In a particular embodiment the organic ligands are ω-hydroxyacids and ω-mercaptoacids ligands.

DETAILED DESCRIPTION OF THE INVENTION

Figure 1:
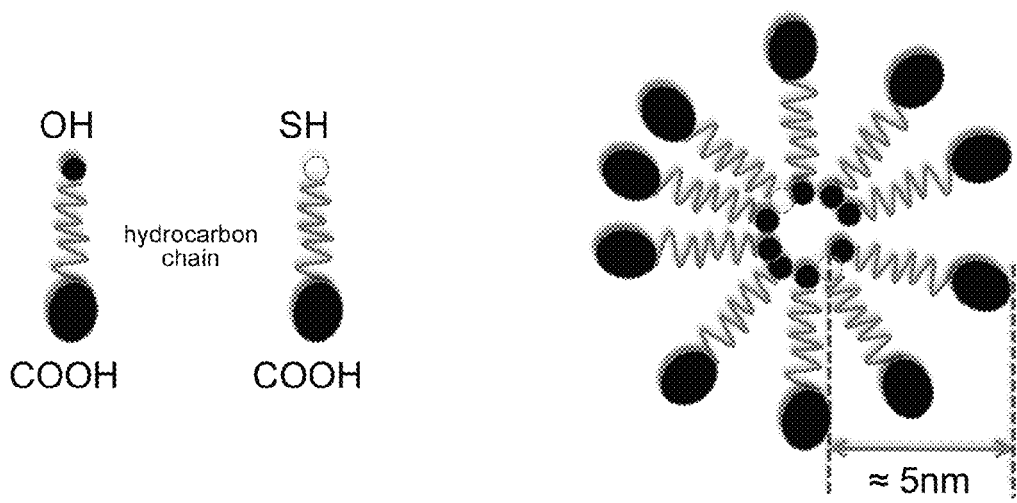
FIG. 1 shows a schematic depiction of a nanosome where the ω-hydroxyacids and ω-mercaptoacids form the monolayer of the nanosome wherein the monolayer has an approximate thickness of 5 nm, it is observed that the acid groups form the outer surface of the nanosome and the hydroxyl, OH, and mercapto, SH, groups face inwards forming the surface of the inner cavity of the nanosome.
Figure 2:
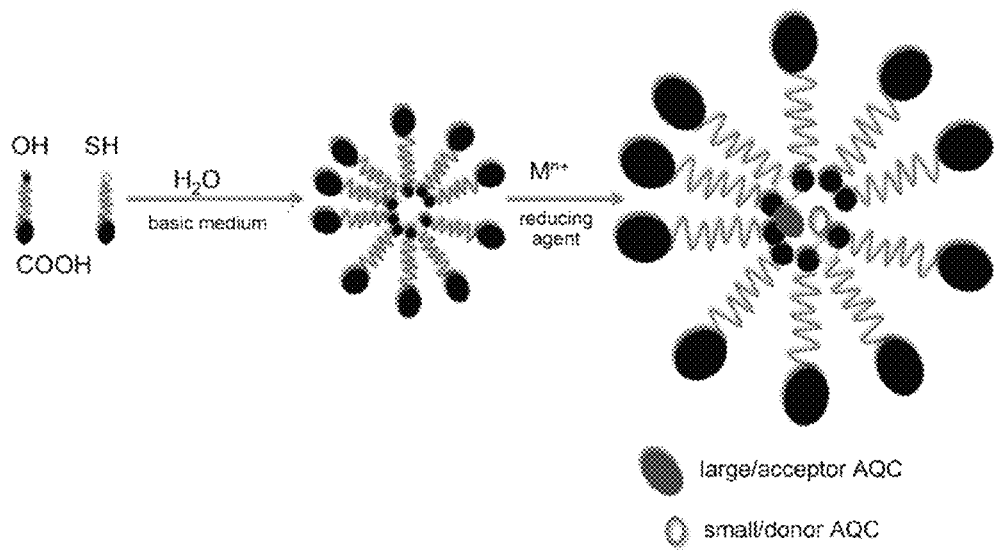
FIG. 2 shows a schematic depiction of the formation of the AQCs inside the nanosystem particularly inside the nanosomes.

The meanings of the terms of the present invention are detailed below.

The term "Atomic Quantum Cluster", abbreviated as AQC, is understood, as said before, as metal Atomic Quantum Cluster. Metal Atomic Quantum Clusters are formed exclusively by zero-oxidation-state metal atoms, in this invention preferably with equal or less than 309 metal atoms. The AQCs are stable over time. Preferably, the AQCs of the invention have sizes comprised between approximately 0.3 and 2.2 nm, preferably between approximately 0.3 and 2 nm, more preferably between approximately 0.3 and 1.8 nm. These metallic AQCs do not longer behave like a "metal" and their behaviour becomes molecular like. Therefore, new properties which are not observed in the nanoparticles, microparticles or metal materials in mass appear in these clusters. Therefore, the physical-chemical properties of the AQC cannot be simply extrapolated from those of the nano/microparticles.

The term "nanocompound" refers herein to a nanometric compound which comprises a charge-transfer complex of general formula (I):

$$M_n^+ M'^-_{n'} \qquad (I),$$

which may, optionally, have organic ligands attached to it. The outer diameter of the nanocompound is approximately equal to or less than 4 nm, preferably equal to or less than 3 nm, more preferably equal to or less than 2 nm. In another embodiment the outer diameter of the nanocompound is equal to or less than 1 nm or equal to or less than 0.6 nm.

The term "charge-transfer complex" also named CT complex, or CTC, or electron-donor-acceptor complex is herein understood as an association of at least two AQCs, in which a fraction of electronic charge, i.e. an electron, is transferred between the AQCs resulting in the formation of the oxidized form of one of the AQCs and the reduced form of the other AQC. The resulting electrostatic interaction, i.e. electrostatic attraction, provides a stabilizing force for the molecular complex. The source AQC from which the charge is transferred is called the electron donor and the receiving AQC is called the electron acceptor. In the present invention:
  $M_n$ is the electron donor, which is the smaller AQC within the complex, and
  $M'_{n'}$ is the electron acceptor, which is the larger AQC within the complex.

The terms "smaller" and "larger" refers comparatively to the number of metal atoms, n and n', of each of the at least two AQCs present at the charge-transfer complex. Therefore, n is smaller than n' (n<n').

In a preferred embodiment, only one electron is transferred between the at least two AQCs, $M_n$ and $M'_{n'}$, therefore resulting the ionic forms, $M_n^+$, i.e. the oxidized form of $M_n$, and $M'_{n'}^-$, the reduced form of $M'_{n'}$, wherein "+" is a positive charge and "−" is a negative charge.

The letters "M" and "M'", in general formula (I), refer to the transition metal of the AQCs. As commented before, "M" and "M'" may be the same or different transition metal. Preferably the transition metal is selected from Au, Ag, Co, Cu, Pt, Fe, Cr, Pd, Ni, Rh and combinations thereof, preferably is selected from Au, Ag, Cu and combinations thereof, and more preferably it is selected from Au, Ag and combination thereof.

In the scope of this invention the term "combination of transition metals" refers to AQCs having atoms of at least two different transition metals as well as to the presence of AQCs of a single transition metal in the presence of AQCs of another transition metal different from the first such that the at least two AQCs of different size can be AQCs with the same transition metal, AQCs with different transition metal, or AQCs with the same or different bimetal combination.

The letters "n" and "n'" refer to the number of transition metal atoms of each AQC. As commented above n is smaller than n' (n<n'). Preferably, the minimum difference between n and n' is five metal atoms. In a preferred embodiment the difference between n and n' is between 5 and 50 atoms, in a particular embodiment the difference between n and n' is between 5 and 25 atoms and in another embodiment the difference between n and n' is between 5 and 15.

The "organic ligands" that may be attached to the charge-transfer complex are at least two different types of organic ligands, and preferably the at least two different types of organic ligands are selected from ω-hydroxyacid (HO—$(CH_2)_m$—COOH) and ω-mercaptoacid (HS—$(CH_2)_p$—COOH) ligands where m and p have a value between 2 and 30, preferably m and p have a value between 10 and 20. In a particular embodiment m and p have a value of 15. In another particular embodiment m and p have a value of 11. The value of m and p can be different or the same. In the event that m and p are different the difference between them is less than 6 carbons, preferably the difference of the values of m and p is between 1 and 4. In a preferred embodiment m and p are the same. Wherein the at least two different types of organic ligands are selected from ω-hydroxyacid (HO—$(CH_2)_m$—COOH) and ω-mercaptoacid (HS—$(CH_2)_p$—COOH) ligands, the acid groups, —COOH, (or —COO$^-$, if the salt of the corresponding acid is used) are directed towards the outer surface of the nanocompound and the —OH and —SH groups directed towards the inside, i.e. towards the ionized AQCs, $M_n^+$ and $M'_{n'}^-$, being bound, attached or coordinated to them.

In another embodiment the "organic ligands" that may be attached to the charge-transfer complex have other functional groups than hydroxyl, —OH, or mercapto, —SH groups, such as —$NH_2$, —NH—, —Cl, —$PH_3$, —SR, —OR, —$NR_2$, —NHR, —NR—, wherein R represents an organic group of a short hydrocarbon chain, $C_1$-$C_4$ capable of bound, attach or coordinate the AQCs or the ionized AQCs, $M_n^+$ and $M'_{n'}^-$. Is also possible exchanging the hydroxyl, —OH, or mercapto, —SH groups of the co-hydroxyacid (HO—$(CH_2)_m$—COOH) and ω-mercaptoacid (HS—$(CH_2)_p$—COOH) ligands with these others, mentioned above that also interact with the metals of the AQCs.

In the context of the present invention, the luminescent nanocompounds described present Stokes shifts greater than approximately 150 nm, preferably greater than approximately 300 nm.

Therefore another aspect of the present invention relates to a method for detecting the nanocompounds described which comprises the steps of:
a) exciting the nanocompund with an external excitation source at an excitation wavelength, $\lambda_{exc.}$, and
b) detecting one or more of the following parameters:
   emission wavelength ($\lambda_{em.}$),
   intensity,
   mean lifetime,
   anisotropy,
   of said nanocompound by suitable detection means.

In a preferred embodiment the method for detecting the nanocompound additionally comprises in that step b) for detecting one or more of the following parameters, emission wavelength, intensity, mean lifetime or anisotropy, is performed with a particular delayed time. This embodiment is based on the fact that the times of half life of the luminescence of the nanocompounds of the invention are greater than 0.1 μs. The delayed time for detecting and measuring one or more of the parameters is greater than 0.1 μs and is preferably greater than 1 μs. Thus, possible interferences due to other emission wavelengths which can be created after excitation with an external excitation source at an excitation wavelength, $\lambda_{exc.}$, in addition to the emission wavelength, $\lambda_{em}$, of the nanocompound object of the present invention, are prevented.

"Exciting" is understood in the scope of the present invention as irradiating the nanocompound with a light radiation of a particular wavelength.

The "suitable detection means" relate to methods for detecting and optionally measuring the indicated parameters known by the person skilled in the art, i.e., methods for detecting the emission wavelength of the luminescence, particularly of the fluorescence, methods for detecting the intensity of the luminescence particularly of the fluorescence, methods for detecting the mean lifetime of the intensity of the luminescence or methods for detecting the anisotropy.

In a particular embodiment, there is no blinking or photobleaching for at least 500 minutes exciting the samples at 300 nm every 30 seconds.

Emission lifetime (τ) which is the luminescence extinction time or the mean lifetime which is the time lapsed since the end of the excitation until the emission intensity reduces to 1/e of the maximum intensity value, i.e. until it reduces to approximately 37%, can be measured. In an embodiment of the present invention the mean lifetime of the luminescence, preferably fluorescence, is greater than 0.1 μs, preferably greater than 1 μs. In a particular embodiment, the nanocompounds have an emission lifetime greater than microsecond for more than 37% of the fluorescence signal.

Another aspect of the invention relates to a method for obtaining the nanocompounds of the invention.

One method comprises the step of preparing aqueous solutions of the AQCs, $M_n$ and $M'_{n'}$. Preferably both solutions have approximately the same concentration of AQCs, i.e. both solutions are equimolar or approximately equimolar. In a further step both solutions are mixed and stirred together to allow the charge-transfer mechanism to occur. In a preferred embodiment the reaction temperature is between 20° C. and 80° C. In another embodiment the reaction time is between 5 minutes and 16 hours.

Another method for obtaining the charge-transfer complex of the invention, particularly the charge-transfer complex which additionally comprises organic ligands, wherein the organic ligands are amphiphilic molecules such as ω-hydroxyacids and ω-mercaptoacids attached to the atomic quantum clusters, $M_n$ and $M'_{n'}$, comprises the following steps:

a) preparing a nanosome by mixing ω-hydroxyacids and ω-mercaptoacids in the presence of a base in aqueous medium, b) adding at least one metal salt to the mixture prepared in step a), c) reducing the mixture obtained in step b), and d) breaking the nanosomes present in the mixture obtained in step c).

The term "nanosome" in the scope of the present invention relates to a nanometric sized vesicle artificially prepared. Thus, the term "nanosome" refers to an spheroid nanometric supramolecular structure formed by one layer of amphiphilic molecules (for example lipids) having two hydrophilic groups bound each one at each end of the aliphatic —($CH_2$)$_n$— chain, or at the antepenultimate, χ, penultimate, ψ, positions of the aliphatic $CH_3$—($CH_2$)$_n$— chain.

The amphiphilic molecules forming said monolayer in the nanosomes of the invention comprise:

a hydrophilic group such as carboxyl (COOH), carboxylate ($COO^-$) or phosphate ($PO_4^-$) group, for example, that are on the outer surface of the vesicle, at one end of the aliphatic chain and substituted at the antepenultimate, χ, penultimate, ψ, positions of the aliphatic $CH_3$—($CH_2$)$_n$— chain, or last, ω, positions of the aliphatic —($CH_2$)$_n$— chain with groups such as for example —OH, —SH, —$NH_2$, —NH—, —Cl, —$PH_3$, —SR, —OR, —$NR_2$, —NHR, or —NR—, wherein R represents an organic group of a short hydrocarbon chain, $C_1$-$C_4$, capable of forming nanosomes which are located towards the inside of the vesicle, at the other end of the aliphatic chain or at the ultimate positions of said aliphatic chain with respect to hydrophilic group, said groups forming the nanocavity with an inner diameter less than or equal to 10 nm, preferably less than or equal to approximately 5 nm, more preferably between 0.8 and 4 nm. In a particular embodiment, the inner diameter of the nanocavity is between approximately 1.5-1.8 nm.

In a preferred embodiment the term "nanosome" refers to a spheroid nanometric supramolecular structure formed by ω-hydroxyacids and ω-mercaptoacids. In this particular embodiment the nanosome comprises ω-hydroxyacids (HO—($CH_2$)$_m$—COOH) and ω-mercaptoacids (HS—($CH_2$)$_p$—COOH) as defined above (see FIG. 1). The ω-hydroxyacids and ω-mercaptoacids present in the nanosome are forming a spherical monolayer with the acid groups, —COOH, (or —$COO^-$, if the salt of the corresponding acid is used) directed towards the outer surface of the nanosystem, i.e. the nanosome, and the —OH and —SH groups directed towards the inside forming an inner cavity in the nanosome such that two approximately concentric spheres are formed, or as referred to in the literature, in the form of fatty acids "bola". This spherical monolayer can have a thickness between approximately 2-10 nm, preferably approximately 5 nm.

The inner cavity of the nanosome is closed. The inner diameter of said inner cavity is less than or equal to 10 nm, preferably less than or equal to approximately 5 nm and more preferably the inner diameter of said inner cavity is between approximately 0.8 and 4 nm. In a particular embodiment the diameter of this inner nanocavity is between approximately 1.5-1.8 nm. In this particular embodiment of the nanosomes, said nanocavity is formed by hydroxyl, —OH, and mercapto, —SH groups, however exchanging these functional groups with others that also interact with the metals, such as —$NH_2$, —NH—, —Cl, —$PH_3$, —SR, —OR, —$NR_2$, —NHR, —NR—, where R represents an organic group of a short hydrocarbon chain, $C_1$-$C_4$ capable of forming nanosomes, is possible.

Tetrabutylammonium hydroxide, tetraoctylammonium hydroxide, triethylbenzylammonium hydroxide, tri-n-octyl-methylammonium hydroxide, trimethyldecylammonium hydroxide, tetramethylammonium hydroxide, tetraethylammonium hydroxide or any other hydroxide having a voluminous group such as a counterion, preferably tetrabutylammonium hydroxide can be used as a base in the step a) of preparing a nanosome by mixing ω-hydroxyacids and ω-mercaptoacids.

In step b) metal salts of transition metals or combinations thereof can be used. Non limiting examples of metal salts are nitrates, sulfates, sulfites, chlorides, bromides, iodides, phosphates, hydroxides, cyanates, carboxylates, thiomalates, thioglucosates of the transition metals. Examples of these metal salts to be used as a single metal salt or in combination with other metal salts are $AgNO_3$, $CH_3COOAg$, $Ag_3AsO_4$, $AgBrO_3$, $AgBr$, $Ag_2CO_3$, $AgClO_3$, $AgCl$, $AgCrO_4$, $AgOCN$, $AgIO_3$, $AgI$, $Ag_2O$, $AgClO_4$, $Ag_3PO_4$, $Ag_2SO_4$, $Ag_2S$, $Ag_2SO_3$, $CuSO_4$, $CuCl_2$, $CuBr_2$, $CuI_2$, $Cu_2S$, $CuSCN$, $CuCN$, $CuCO_3$, $Cu_2O$, $Cu(OH)_2$, $Cu(NO_3)_2$, $Cu(ClO_4)_2$, $Cu(HCO_2)_2$ or $Cu(CO_2CH_3)_2$. Non-limiting examples of gold metal salts to be used in combination, are $HAuCl_4$, $AuCl$, $AuCl_3$, $HAuCl_4$, $HAuCl_4$.aq, $KAuCl_4$, $LiAuCl_4(CH_3)_2SAuCl$, $C_3H_9AuClP$, $C_6H_{15}AuClP$, $C_{18}H_{15}AuClP$, $C_8H_{11}AuClP$, $C_5H_5AuCl_3N$, $(C_4H_9)_3PAuCl$, $C_{27}H_{36}AuClN_2$, $C_{21}H_{12}AuClF_9P$, $C_{20}H_{27}AuClP$, $C_{33}H_{49}AUClP$, $C_{42}H_{63}AuClO_3P$, $C_{21}H_{24}AUClN_2$, $C_{35}H_{49}AuF_6NO_4PS_2$ or $(C_{20}H_{15}AuF_6NO_4PS_2).2C_7H_8$.

Non-limiting examples of reduction systems or reducing agents to be used in step c) for reducing the mixture obtained in step c) can be $NaBH_4$, DIBAH, LiAlH4, $N_2H_4$ or $SnCl_2$ and also gentler reducing agents such as sodium hypophosphite, amines, sugars, organic acids, polymers such as polyvinylpyrrolidone, UV-VIS radiation, ultrasounds and photoreduction.

After the steps b) and c) of the present method, "nanosomes comprising AQCs" are formed. These "nanosomes comprising AQCs" comprise inside their inner cavity, i.e. encapsulated, the AQCs of at least two different sizes, i.e. $M_n$ and $M'_{n'}$.

A particular example of these "nanosomes comprising AQCs" is described in Gaillard, C., *Journal of Colloid and Interface Science*, Vol. 337, 2, 610-613, which describes gold particle synthesis inside these nanosystems.

The step of breaking down the nanosomes is a desestabilization process of the previously synthesized nanosomes. This step may be accomplished by different mechanisms. In a preferred embodiment the step of breaking the nanosomes, or destabilize the nanosomes, is made by means of ultracentrifugation, but any other means known in the art may be also useful for breaking the nanosomes, such as a thermal treatment or pH variation. The charge-transfer mechanism takes place during the step of breaking down the nanosomes. The nanosome is therefore destabilized and the charge-transfer complex of general formula (I) is formed.

In the scope of the present invention it is also possible to obtain the charge-transfer complex by breaking other nanosystems other than nanosomes which comprise in their inner cavities AQCs of at least two different sizes, i.e. $M_n$ and $M'_{n'}$.

The term "nanosystem" refers to an spheroid-like nanometric supramolecular structure formed by one or two layers of amphiphilic molecules, wherein said amphiphilic molecules form a nanocavity at the inside of the nanosystem. Particularly, the nansosytem having an outer diameter approximately equal to or less than 20 nm, preferably equal to or less than 18 nm and more preferably equal to or less than 15 nm. The inside of the nanosystem comprised at least one nanocavity with an inner diameter less than or equal to 10 nm, preferably less than or equal to approximately 5 nm, more preferably between 0.8 and 4 nm. In a particular embodiment, the inner diameter of the nanocavity is between approximately 1.5-1.8 nm. Non-limiting examples of nanosystems are nanosomes but also micelles, reverse micelles, nanoemulsions or microemulsions. In a preferred embodiment the nanosystem is a nanosome.

The expression "spheroid-like" means that it has a solid geometrical figure similar in shape to a sphere.

The amphiphilic molecules forming the nanosystems may be the same or different, preferably two different type of molecules, and each molecule possess both hydrophilic and lipophilic properties.

The lipophilic properties are given by a group which is typically a hydrocarbon moiety, such as an aliphatic chain of the form $CH_3-(CH_2)_n-$ or $-(CH_2)_n-$ being 30>n>2, preferably 20>n>10.

The hydrophilic properties are given by a hydrophilic group. The hydrophilic group may be a charged group or a polar uncharged group. The charged group is selected from anionic groups, preferably is selected from the group formed by carboxylates, sulfates, sulfonates and phosphates. The polar uncharged group is selected from the group formed by $-OH$, $-SH$, $-NH_2$, $-NH-$, $-Cl$, $-PH_3$, $-SR$, $-OR$, $-NR_2$, $-NHR$ and $-NR-$, wherein R represents an organic alkyl group of a short hydrocarbon chain, $C_1$-$C_4$, preferably methyl, ethyl or propyl group.

The amphiphilic molecules may have one aliphatic $CH_3-(CH_2)_n-$ chain and one hydrophilic group bound to it or two hydrophilic groups bound each one at each end of the aliphatic $-(CH_2)_n-$ chain.

The term "micelle" refers to amphiphilic molecules aggregates. In an aqueous medium, the lipophilic domains of the molecule aggregate are oriented towards the inside of the micelle and the hydrophilic domains are in contact with the medium. In "reverse micelles" the molecules are organized such that the lipophilic region is exposed to the outside and the hydrophilic region to the inside. In the state of the art the term "microemulsion" is also used to refer to a "reverse micelle", i.e. the "microemulsion" is a particular embodiment of a "reverse micelle". The term "microemulsion" refers to a system of at least three components (water, organic solvent-known commonly as oil- and amphiphilic compound), single phase and thermodynamically stable, formed by nanometric sized droplets. Although not restrictive, the use of water-in-oil microemulsions wherein water droplets are dispersed in the organic medium is of particular interest for the present invention. Among these water-in-oil microemulsions, the use of polymerized microemulsions relating to microemulsions containing acrylic monomers, for example acrylamide or 1,6-hexanediol diacrylate inside the water droplets which are polymerized by means of introducing some initiator, such as for example a radical photoinitiator, is also of interest due to its stability. Thus, the microemulsion droplets can become more resistant.

The term "nanoemulsion" refers to a system of at least three components (water, organic solvent and stabilizing compound), two-phase and thermodynamically unstable but is temporary stabilized by chemical or physical processes and is formed by nanometric droplets. The formation of nanometric droplets is the only thing that differentiates the nanoemulsions from the emulsions known in the state of the art, therefore the term "nanoemulsion" generally refers to an emulsion in which the droplets are of nanometric size.

In a particular embodiment the nanosystem is selected from the group formed by nanosome, micelle and reverse micelle, preferably the nanosystem is a nanosome.

In the particular embodiment wherein the nanosystem is a reverse micelle, the reverse micelle comprises at least two different surfactants, wherein at least one comprises a thiol or thioether group as its polar group. In a more particular embodiment, the at least two surfactants are an alcohol ethoxylate and a ω-mercaptoacid.

The inner cavity of the nanosystem is closed. As mentioned above, the inner diameter of said inner cavity is less than or equal to 10 nm, preferably less than or equal to approximately 5 nm and more preferably the inner diameter of said inner cavity is between approximately 0.8 and 4 nm. In a particular embodiment the diameter of this inner nanocavity is between approximately 1.5-1.8 nm.

An approximate estimation of the cluster excitation and emission wavelengths can be determined by approximation by means of the Jellium model (see J. Calvo et al., *Encyclopedia of Nanotechnology*, Ed. by B. Bhushan, Springer Verlag, 2011, for example). This model predicts in a rather approximate manner the prohibited energy bandgap of the clusters and, therefore, the position of the emission bandgap thereof. The excitation bandgap of the clusters can in turn be predicted from the emission bandgap taking into account that the Stokes shift in clusters of a particular size is of approximate 50-100 nm. The following table, Table 1, shows the theoretical data for AQCs of Au or Ag according to this mode, i.e., the approximate excitation $\lambda_{exc.}$ and emission, $\lambda_{em.}$, wavelengths have been calculated with an error of ±50 nm in AQCs of Au or Ag by means of said Jellium model: $E_{em}=E_F/N^{1/3}$; where $E_{em}$=emission energy; N=no. of atoms in the AQC; and $E_F$=Fermi level which is the same approximately 5.5 eV for gold and silver.

TABLE 1

| Cluster | $\lambda_{exc.}$ (nm) | $\lambda_{em.}$ (nm) |
|---|---|---|
| $A_2$ | 200-250 | 300 |
| $A_3$ | 240-290 | 340 |
| $A_4$ | 270-320 | 370 |
| $A_5$ | 300-350 | 400 |
| $A_6$ | 325-375 | 425 |
| $A_7$ | 350-400 | 450 |
| $A_{10}$ | 400-450 | 500 |
| $A_{12}$ | 440-490 | 540 |
| $A_{15}$ | 475-525 | 575 |
| $A_{20}$ | 535-585 | 635 |
| $A_{25}$ | 580-630 | 680 |
| $A_{30}$ | 630-680 | 730 |
| $A_{40}$ | 700-750 | 800 |

These values can also vary in practice when the nanosystem is made to react to exchange the OH and SH groups with other ligands in the inner cavity of the nanosystem. Without being limiting, the ligands to be exchanged can be chosen from $-NH_2$, $-NH-$, $-Cl$, $-PH_3$, $-SR$, $-OR$, $-NR_2$, $-NHR$, $-NR-$, where R represents a short chain organic group capable of forming nanosomes.

In other words, the type of clusters to be used to obtain a particular excitation and emission wavelength can be decided from the table above. Thus, for example, to obtain a system with an excitation wavelength at 300 nm, an emission wavelength at 600 nm and a Stokes shift of 300 nm, the following cluster sizes should be selected:

excitation cluster ("donor", $M_n$): $M_3/M_5$,
emission cluster ("acceptor", $M'_n$): $M'_{12}/M'_{20}$.

Figure 6:
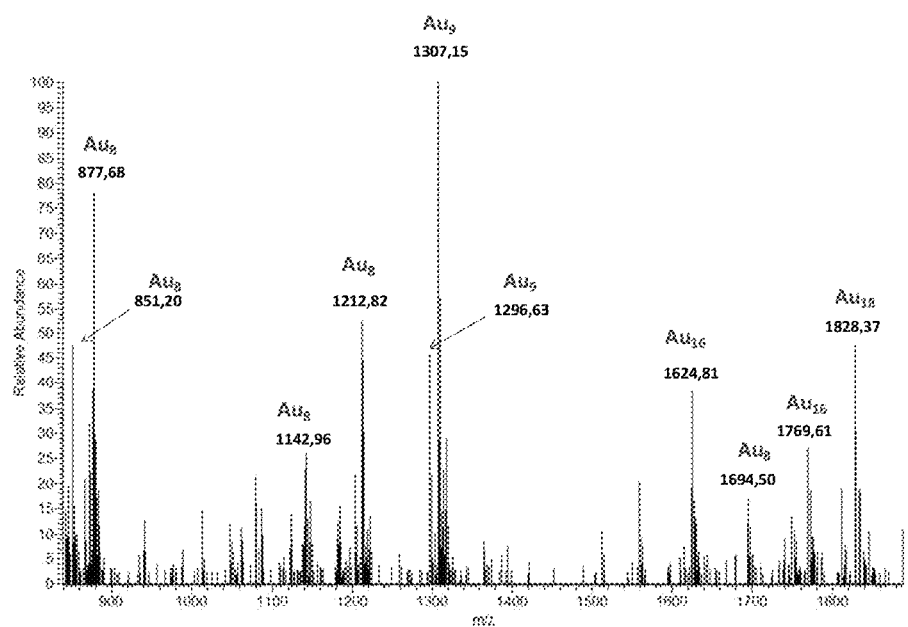
FIG. 6 shows the ESI-orbitrap mass spectrum for the charge-transfer complex obtained in Example 1.

This was experimentally confirmed for the Example 1, by mass spectrometry (FIG. 6 where signals for $Au_8/Au_9$ and $Au_{18}/Au_{20}$ were found, both near the range of the predicted AQCs.

As used herein, the term "approximately" means a slight variation from the specified value, preferably within 10 percent of the specified value. However, the term "approximately" may mean a greater variation tolerance depending on, for example, the experimental technique used. The person skilled in the art understands said variations of a specified value and they are within the context of the present invention. Furthermore, in order to provide a more precise description, some of the quantitative expressions provided in the present document are not described with the term "approximately". It is understood that, the term "approximately" is explicitly use or otherwise, each amount given in the present document attempts to refer to the actual given value, and it also attempts to refer to the approximation of such given value which would be reasonably deduced based on the common knowledge in the art, including equivalents and approximations due to experimental conditions and/or from measurement for such given value.

EXAMPLES

Example 1

Synthesis of $Au_{8-9}$-$Au_{18-20}$ Charge-Transfer Complex

Firstly, stock solutions of 12-mercaptododecanoic acid and 12-hydroxydodecanoic acid are prepared at a concentration of 10 mg/ml, a given volume of tetrabutyl ammonium hydroxide solution (1.5 M in water) is added to ensure a molar ratio of fatty acid/TBAOH of 1. Then nanosomes are prepared mixing a given volume of each fatty acid stock solution with 25 ml of pure water (3.6 ml of 12-mercaptododecanoic acid and 10 ml of 12-hydroxydodecanoic acid).

In a second step, a stock solution of 0.0147 M $HAuCl_4$ is prepared in pure water. Then 2.7 ml of this solution is poured in the nanosome sample. An extra amount of TBAOH solution is added to the mixture to ensure redispersion of the material. Then, 2.7 ml of a freshly prepared stock solution of 0.05 M $NaBH_4$ is added to the sample dropwise under vigorous agitation. The reaction is finished after 1 hour stirring at 35° C. in a thermostatted bath.

Then, a solution of the Au AQCs nanosomes obtained before was ultracentrifugated during one hour at 90000 rpm, obtaining the $Au_{8-9}$-$Au_{18-20}$ charge-transfer complex as the supernatant of the separation.

Figure 5:
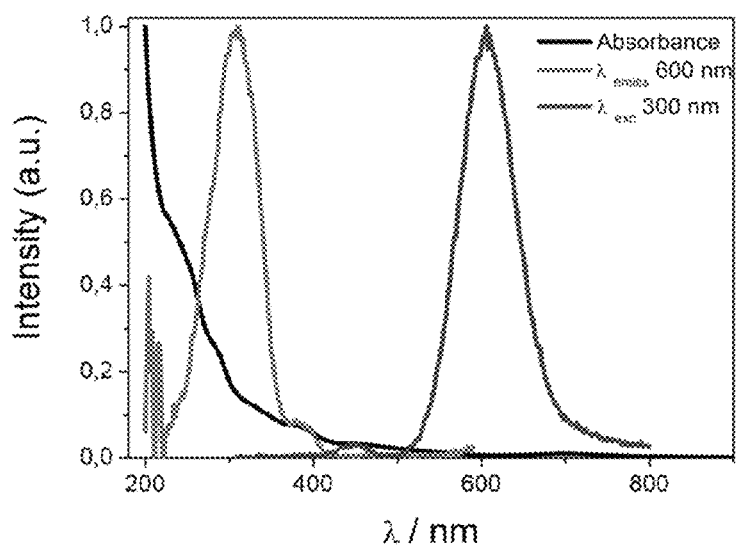
FIG. 5 shows the optic properties of the charge-transfer complex obtained in Example 1.

The fluorescent properties of $Au_{8-9}$-$Au_{18-20}$ charge-transfer complex are shown in FIG. 5, showing a Stokes shift of 300 nm. FIG. 6 shows the ESI-Orbitrap mass spectrum, where peaks for $Au_8$, $Au_9$, $Au_{18}$ and $Au_{19}$ were found.

Example 2

Synthesis of $Au_{13}$-$Au_{25}$ Charge-Transfer Complex

Figure 3:
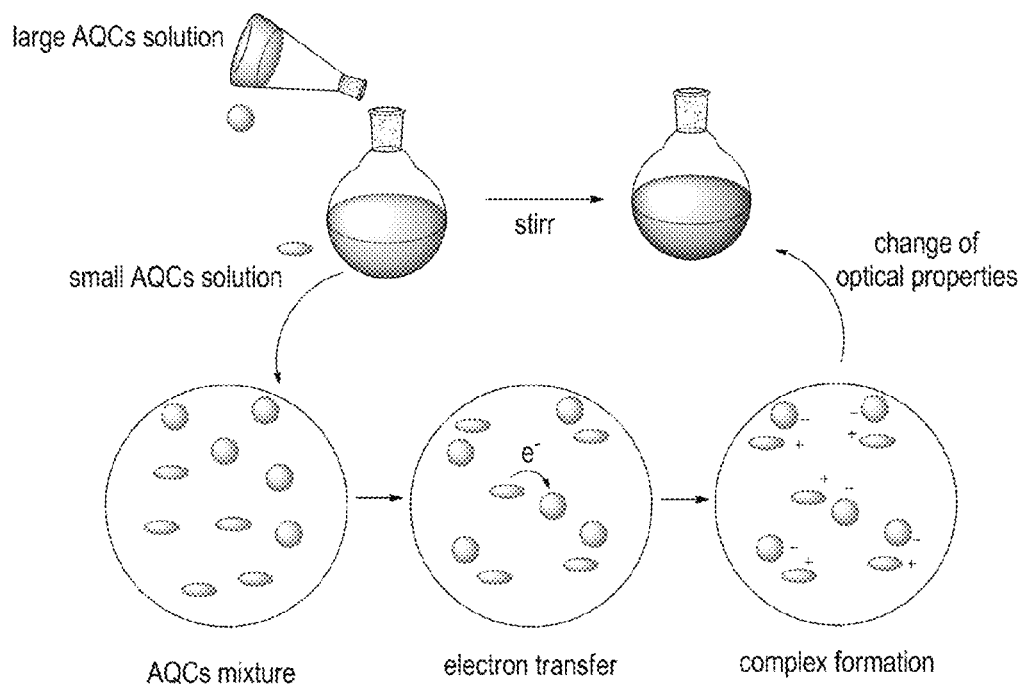
FIG. 3 shows the method for obtaining a charge-transfer complex without ligands attached to it and the charge-transfer mechanism.
Figure 4:
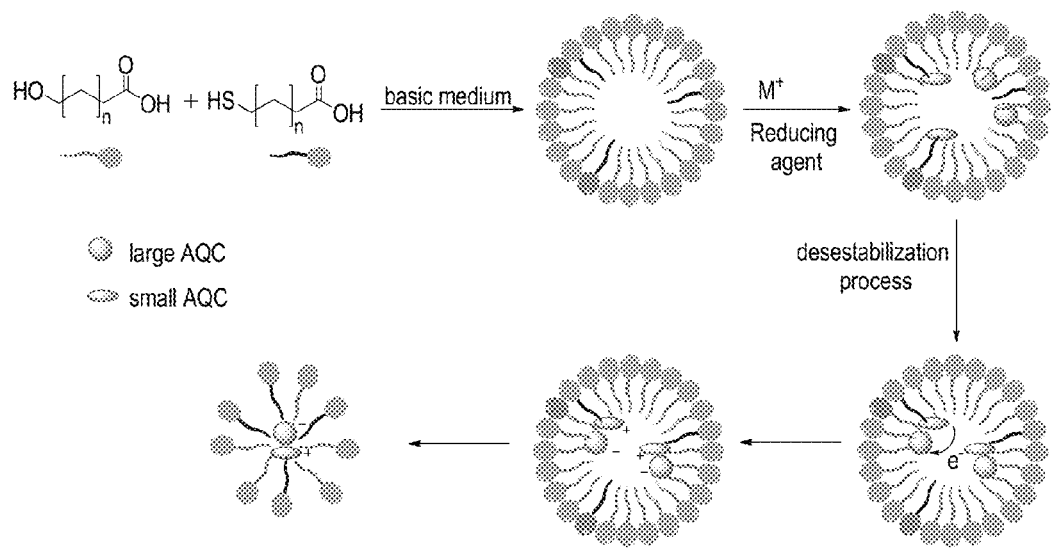
FIG. 4 shows the method for obtaining a charge-transfer complex with ligands attached to it and the charge-transfer mechanism.

Mix and stir overnight equivalent volumes of two equimolar, $Au_{13}$ and $Au_{25}$, aqueous AQCs solutions (0.1 mM en water), as shown in FIG. 3.

Examples of the synthesis of $Au_{13}$ and $Au_{25}$ AQCs are found, for example in Abad, J. M. et al., J. Am. Chem. Soc. 2007, 129 (43), 12932-12933; and Shichibu, Y. et al., J. Am. Chem. Soc. 2005, 127 (39), 13464-13465.

The invention claimed is:

1. A charge-transfer complex of at least two different size metal atomic quantum clusters (AQCs), $M_n$ and $M'_{n'}$, of general formula (I):

$$M_n^+ M'_{n'}^- \qquad (I),$$

wherein
the metals, M and M', of the metal AQCs are the same or different metals,
$M_n$, is the smaller AQC which is present in its oxidized form, $M_n^+$,
$M'_{n'}$ is the larger AQC which is present in its reduced form, $M'_{n'}^-$,
$M_n^+$ and $M'_{n'}^-$ are bound by electrostatic interactions,
n and n' are respectively the number of metal atoms of M and M', and
n is smaller than n'.

2. The charge-transfer complex according to claim 1, wherein the same or different metals, M and M', of the metal atomic quantum clusters are selected from transition metals or combinations thereof.

3. The charge-transfer complex according to claim 1, wherein the same or different metals, M and M', of the metal atomic quantum clusters are selected from the transition metals Au, Ag, Cu and combinations thereof.

4. The charge-transfer complex according to claim 1, wherein the number of metal atoms, n and n', of the at least two different size metal atomic quantum clusters are characterized by being made up of:
between 2 and 309 metal atoms,
between 2 and 102 metal atoms,
between 2 and 55 metal atoms, or
between 2 and 25 metal atoms.

5. The charge-transfer complex according to claim 1, wherein the difference between n and n' is between 5 and 50 atoms.

6. The charge-transfer complex according to claim 1, additionally comprising ω-hydroxyacids and ω-mercaptoacids ligands attached to the atomic quantum clusters, $M_n$ and $M'_{n'}$.

7. A luminescent detection process, comprising disposing a charge-transfer complex in a potential interaction environment, and luminescently detecting the charge-transfer complex in said environment producing detectable luminescence, wherein said charge-transfer complex comprises a charge-transfer complex as defined in claim 1.

8. The process according to claim 7, wherein the luminescence is obtained after an excitation of the charge-transfer complex by an external excitation source.

9. The process according to claim 8, wherein the luminescence is fluorescence.

10. The process according to claim 7, wherein the Stokes shift is greater than approximately 150 nm.

11. The process according to claim 7, wherein the luminescence has a decaying time greater than 0.1 μs.

12. A method for detecting in a detection environment a charge-transfer complex as defined in claim 1, said method comprising the steps of:
a) exciting the charge-transfer complex with an external excitation source at a predetermined excitation wavelength ($\lambda_{exc.}$), and
b) detecting one or more of the following parameters of said charge-transfer complex by a detection apparatus:
emission wavelength ($\lambda_{em}$),
intensity,
mean lifetime, and
anisotropy.

13. A method for obtaining a charge-transfer complex as defined in claim 1, comprising the steps of:
   a) preparing an aqueous solution of the smaller AQC, $M_n$,
   b) preparing an aqueous solution of the larger AQC, $M'_{n'}$, and
   c) mixing together the aqueous solution of the smaller AQC with the aqueous solution of the larger AQC.

14. A method for obtaining a charge-transfer complex as defined in claim 6 comprising the steps of:
   a) preparing a nanosome by mixing ω-hydroxyacids and ω-mercaptoacids in the presence of a base in aqueous medium,
   b) adding at least one metal salt to the mixture prepared in step a), and
   c) reducing the mixture obtained in step b), and
   d) breaking the nanosomes present in the mixture obtained in step c).

15. The method of claim 14 wherein the step of breaking the nanosomes is made by ultracentrifugation.

16. The charge-transfer complex according to claim 1 wherein the same or different metals, M and M', of the metal atomic quantum clusters are selected from Au, Ag and combinations thereof.

17. The process according to claim 7, wherein the Stokes shift is greater than 300 nm.

18. The process according to claim 7, wherein the luminescence has a decaying time greater than 1 μs.

* * * * *